(12) United States Patent
Jansen et al.

(10) Patent No.: US 7,479,248 B2
(45) Date of Patent: Jan. 20, 2009

(54) VESSEL PROSTHESES OR PATCHES MADE FROM BIOCOMPATIBLE POLYMERS

(75) Inventors: Josef Jansen, Köln (DE); Engin Kocaman, Baesweiler (DE)

(73) Assignee: Adiam Life Science AG, Erkelenz (DE)

( * ) Notice: Subject to any disclaimer, the term of this patent is extended or adjusted under 35 U.S.C. 154(b) by 196 days.

(21) Appl. No.: 10/529,814

(22) PCT Filed: Sep. 17, 2003

(86) PCT No.: PCT/DE03/03079

§ 371 (c)(1),
(2), (4) Date: Oct. 3, 2005

(87) PCT Pub. No.: WO2004/028581

PCT Pub. Date: Apr. 8, 2004

(65) Prior Publication Data

US 2006/0122699 A1 Jun. 8, 2006

(30) Foreign Application Priority Data

Sep. 20, 2002 (DE) ................ 102 43 967

(51) Int. Cl.
*B29C 55/04* (2006.01)
*B29C 55/12* (2006.01)
*B29C 55/22* (2006.01)

(52) U.S. Cl. ............... 264/562; 264/563; 264/565; 264/288.8; 264/289.3; 264/289.6; 264/290.2

(58) Field of Classification Search ............ 264/288.8, 264/289.3, 289.6, 290.2, 562, 563, 565
See application file for complete search history.

(56) References Cited

U.S. PATENT DOCUMENTS

| 5,197,976 A | * | 3/1993 | Herweck et al. | 623/1.27 |
| 5,254,662 A | * | 10/1993 | Szycher et al. | 528/67 |
| 6,743,388 B2 | * | 6/2004 | Sridharan et al. | 264/205 |

* cited by examiner

*Primary Examiner*—Suzanne E. McDowell
(74) *Attorney, Agent, or Firm*—Andrew Wilford

(57) ABSTRACT

The invention relates to a vessel prosthesis or patch, made from a biocompatible polymer with microporous, finely-fibrillated structure and a method for improving the e-modulus of said vessel prostheses or patches. According to the invention, the vessel prostheses or patches are subjected to a full stretching (extension) with a degree of extension between 30% and 250% and subsequent restoration.

10 Claims, 1 Drawing Sheet

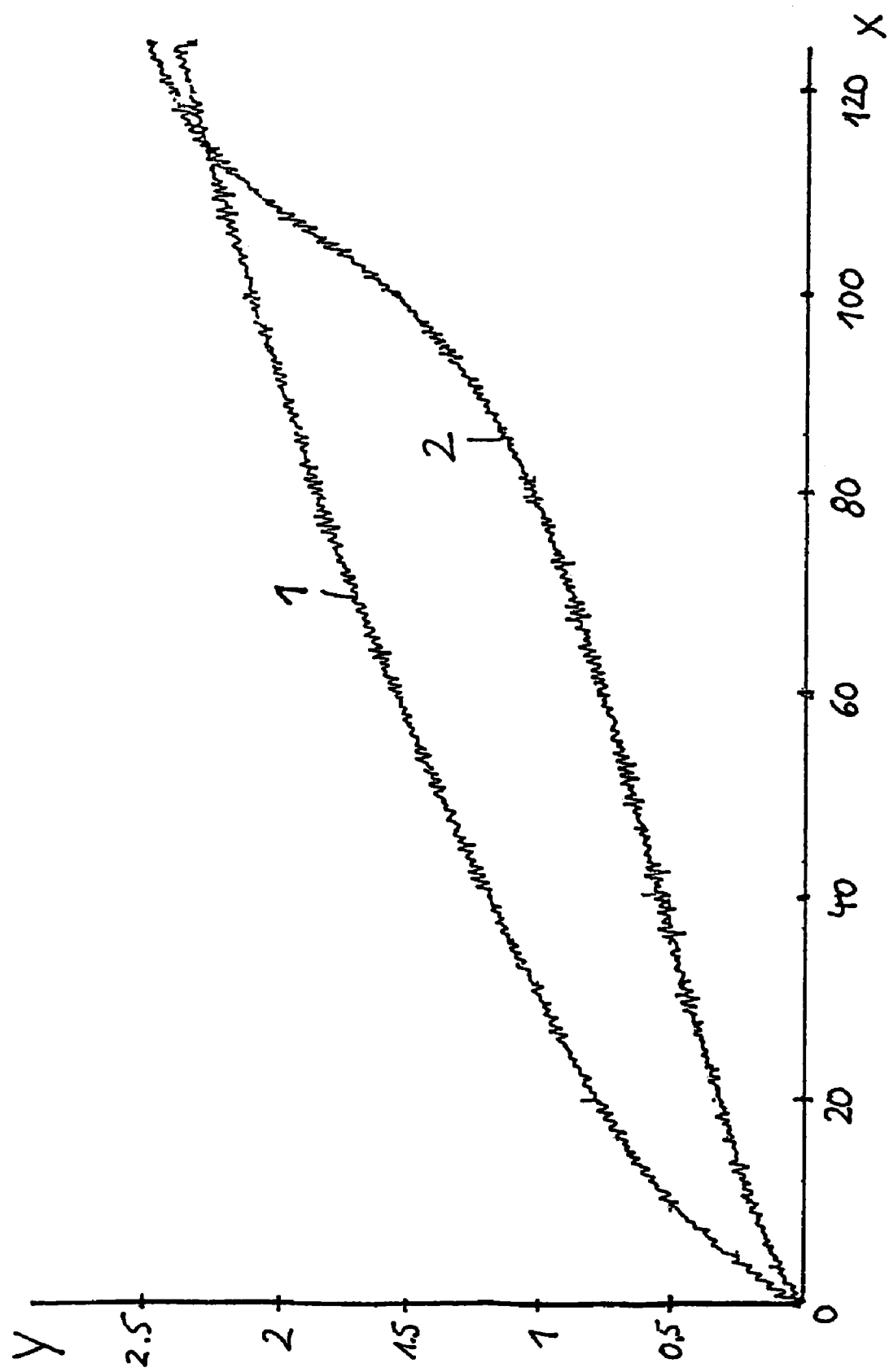

VESSEL PROSTHESES OR PATCHES MADE FROM BIOCOMPATIBLE POLYMERS

The invention relates to a vessel prosthesis or a tissue patch with a microporous finely fibrillar structure of a biocompatible polyurethane, especially of polyurethane, polyamide, polysulfone, polyester, isotactic polypropylene, polynitrile and/or polyvinylchloride, or mixtures thereof or copolymers thereof, as well as to a method of improving the modulus of elasticity (E-modulus) of such a workpiece.

Small-lumen vascular prostheses with diameters below 4 mm have not been available on the market up to now. The development of such vessels requires, as previously, considerable effort. All previous investigators have found that fabricated vessels of these sizes tended, through thrombolytic deposits and hyperplasia, to become prematurely blocked.

Also the tissue patches known in the state of the art which have been used in cases of tissue defects have been found to be not compatible to the desired degree with natural tissue.

It is, therefore, the object of the present invention to provide vascular prostheses, especially small-lumen vascular prostheses, or tissue patches which have such a differentiated natural structure that a largely physiological, axial and tangential elasticity (compliance) can be achieved. According to a further object of the invention the vascular prostheses and tissue patches should have degrees of openness which permit the ingrowth and formation of a thin and stable neointima.

The physiological compliance is important for the degree of openness (openness rate) of the vessel as can be seen from Salacinski et al.: "The mechanical behavior of vascular grafts," Journal of Biomaterials Applications, Vol. 15, January 2001, pages 241 ff. and "Cardiovascular biomaterials," Garth W. Hastings, 1991, Chapter 1, pages 1-16, "Mechanical Properties of Arteries and Arterial Grafts," T. V. How.

Surprisingly, the elasticity or the modulus of elasticity (E-modulus) of vascular prostheses or tissue patches of biocompatible polymers can be improved when these are subjected to a definitive (conclusive, decisive) full stretching (extension) with a degree of extension of 30% to 250%, preferably 60% to 125%, and subsequent restoration (relaxation or relief). This result is surprising since extension of material samples in a film form which is significantly above the elastic range has been found to harden the polymer, that is to increase the modulus of elasticity. Such an effect has been described in "Porous polyurethane vascular prostheses with variable compliances," by Shu Qin Liu and Makoto Kodama in Journal of Biomedical Materials Research, Vol. 26, 1489-1502 (1992).

If, however, the polymer has a microporous finely fibrillar structure, the E-modulus of the vessel or patch is reduced. The microporous, finely fibrillar polymer structure is achieved when the process described in DE 28 06 030 C2 is used, whereby the polymer is spun from a solution by means of nozzles to microfibers. The thus-produced fibrils are wound in several hundred layers under defined angles on forms and at their cross-over points are fused together layer-wise with one another so that vessels and patches are made which are mechanically and biologically stable microporous structures.

The inner side of the vessel or the patch turned toward the blood should be a smooth as possible, whereas the outer side can have a rough configuration since in many cases a desirable surface quality of the synthetic blood-vessel prosthesis should correspond to that which will ensure a rapid growth of binder tissue onto the blood-vessel prosthesis after its implantation to thereby fix this prosthesis in position.

Since a vessel or patch which has been subjected to the definitive or decisive stretching, by comparison with workpieces that have not been subjected to such treatment, have a previously unattainable ultrasoft and flexible material structure, the vessels and patches of the invention have longitudinal and transverse elasticity resembling that of the natural tissue. The exceptionally high compliance for vascular prostheses means that they will conduct the pulse waves of the blood physiologically in the sense of a surge tank as can be seen in canine carotis-interponates and femoralis-interponates in the triphasic flow velocity amplitude. In such prostheses a laminar flow should be maintained so that it is possible to avoid the caliber jump which was to be feared with known vascular prostheses and which might have led to blood-damaging turbulence at anastomoses with progressive cavitation and dead-flow regions and the formation of hyperplasias. With the flexible material structure produced with the definitive stretching, the vessels and patches have an especially good shape retentiveness for optimum flow [rheological] properties with good anti-buckling stability upon the development of an internal pressure.

The polymers used should above all be soluble in a solvent, preferably an organic solvent, so that they can be spun from specially provided nozzles to fine threads or fibers.

Preferred groups of materials which can be used are polyurethanes, polyamides, polysulfones, polyesters, isostatic polypropylenes, polynitriles and/or polyvinylchlorides. Also copolymers of these groups can be used as well as further variants of these groups such as segmented polymers like, for example, polyurethanes equipped with, for example, hard and soft segments.

Depending upon the use, it is advantageous to stretch the vessel or the patch in the longitudinal and transverse directions uniformly or to impart a preferred stretch direction to it, for example to make the vessel or the patch softer in the longitudinal direction than in transverse direction. By applying different degrees of extension to the vessel or patch in both directions, the properties of a workpiece can be substantially matched to the natural structures.

Depending upon the material type of the polymer used and upon the draw-off speed and particular stretching parameters, there will be a practically complete restoration or relaxation or a restoration with a slight remaining extension of 3 to 5% which, according to a feature of the invention, is considered in that the pore size of the vascular prosthesis or the tissue patch before the stretching may be made smaller by the expected nonrecoverable degree of extension, especially for vessels which are to have a certain pore size which is desirable for the growth of cells into these pores, or where the patches or the vascular prostheses are initially smaller than their final size so that the stretching will yield the desired width.

According to the invention, different stretching methods or extension methods can be used. Apart from a uni-axial or bi-axial extension of the patch or vessel that can be carried out with a conventional tensile testing machine, tubular vascular prostheses can also be stretched by internal pressurization with a gaseous medium like air or nitrogen, or with a liquid medium.

If leakage, which can arise naturally because of the porosity of the vessel, is to be avoided, the pressure application can be effected through a yieldable, preferably elastic, auxiliary body which is inserted into the vascular prosthesis before the stretching and is then pressurized. The method according to the invention can also be so carried out that the vascular prosthesis or the tissue patches, prior to stretching, are immersed in a water-soluble physiological substance, preferably polyvinylalcohol (PVA), polyvinylpyrrolidone or gelatine (collagen) with a corresponding viscosity. This substance penetrates fully or partly into the fleece of the vascular prosthesis or the tissue patch, preferably on the outer side of the fleece material. Within the scope of the present invention it is, however, also possible to seal the vessel internally or externally or also in an intermediate layer by an additional liquid-impermeable layer which is built into it.

Especially for the stretching of tissue patches, in accordance with a further feature of the invention, an auxiliary body of mechanically adjustable size can be provided, on which the tissue patch is clamped or which can be inserted in the tubular prosthesis. The auxiliary body can be an elastic component that is shoved into the vessel in a folded-up state and is then expanded and thereafter permitted to return to an original size in the sense of a spring or expander. Alternatively a multiplicity of thin rods can also be inserted into a tubular vascular prosthesis body and then pressed radially outwardly for widening the vessel. Finally tubular vascular prostheses can also be widened or expanded by a widening mandrel which is insertable therein.

Tests carried out on polyurethane sample bodies have shown that the E-modulus is up to 50% less after the stretching.

A usable polyurethane can be obtained by reacting at least one aliphatic and/or at least one cycloaliphatic diisocyanate with a macrodiol of the polycarbonate, polyester, polyether, polysiloxane or polysulfone type with an average molecular weight of 500 to 6000 and reacting the prepolymer thus obtained further with a chain-lengthening agent represented by a low molecular weight diol or a mixture of a low molecular weight diol with a macrodiol of the polyester, polyether, polysiloxane or polysulfone or polycarbonate type with an average molecular weight of 500 to 6000, the ratio of NCO terminal groups of the prepolymer to OH groups of the chain lengthening agent amounting to 1.01:1 to 1.05:1, and subjecting the obtained polymer, optionally after a treatment with a reagent to deactivate still-present NCO groups, to a molecular weight fractionation in which the unusable low molecular weight polyurethane portion making up the mass proportion of 10 to 55 percent by weight is separated off and optionally discarded, and the remaining high molecular weight fraction is recovered as the biocompatible polyurethane with improved properties.

As aliphatic diisocyanates, straight chain or branched $C_2$ to $C_{10}$ alkyl diisocyanates are suitable which are substituted with methyl, ethyl, n-propyl, isopropyl or butyl. Preferably $C_4$ to $C_8$ alkyl isocyanates are used and especially preferred are $C_5$ to $C_6$ alkyl isocyanates, which can respectively be substituted with methyl, ethyl n-propyl, isopropyl or butyl. Especially preferred are hexane diisocyanates which can be substituted with methyl residues. In detail, the following specific compounds can be mentioned, 1,6-diisocyanate-2,2,4-tetramethyl-hexane, 1,6-diisocyanato-2,4,4-trimethylhexane and 1,6-diisocyanato-2,2,4-trimethyl-hexane.

As cyclo aliphatic diisocyanates, the ones containing cyclobutyl, cyclopentyl, cyclohexyl, cycloheptyl, cyclooctyl, cyclomonyl or cyclodecl groups are suitable and the cycloaliphatic residues can be linked by one or more methylene residues. Preferred are cyclopentylmethane-diisocyanate, cyclohexyl methane diisocyanate and dicyclohexyl-methanediisocyanate. Especially preferred are cyclohexane-methane-diisocyanate and dicyclohexylmethanediisocyanate. In detail, the 4,4, dicyclo hexylmethane diisocyanate, the 1,4-cyclohexyldiisocyanate, the 1,3-bis (isocyanatomethyl) cyclohexane, the 1,4-bis-(isocyanatomethyl)-cyclohexane and isophorondiisocyanate are especially mentioned even more preferred for the method of the invention is the use of 4,4'-dicyclohexylmethanediisocyanate and 1,4-cyclohexyldiisocyanate. It will be self understood that isomer mixtures of the named diisocyanates are also suitable.

As the macro dioles, suitable are polyesters, pblyethers, polysiloxanes, or polysulfone which have two OH terminal groups and are of an average molecular weight of $M_w$=500 to 6000 (Mw=molecular weight measured in Daltons), preferably polyesters, polyethers, polysiloxane and polysulfone with two OH terminal groups with a mean molecular weight of $M_w$=500 to 4000 (Mw=mean molecular weight–Daltons), while especially preferred are polyesters, polyethers, of polysiloxanes or polysulfones with two OH terminal groups and a mean molecular weight of $M_w$=1000 to 3000 ($M_w$=mean molecular weight e.g. in Daltons) and especially preferred are polyesters, polyethers polysiloxanes and polysulfones with two terminal OH groups and an average molecular weight of $M_w$=1000 to 2400 ($M_w$=average molecular weight-Daltons). As polyesters, those which can be mentioned have $C_1$ through $C_{10}$ alkylene building blocks and preferably with such $C_2$ to $C_6$ alkylene building blocks with especially preferred being those with $C_2$ to $C_4$ alkylene building blocks, each being substitutable with methyl groups.

As the polyethers those which can be mentioned are those with $C_1$ through $C_{10}$ alkylene building blocks, preferably those with $C_2$ to $C_6$ alkylene building blocks and especially those with $C_2$ through $C_4$ alkylene building blocks.

As polysiloxanes those which can be mentioned have $C_1$ through $C_{10}$ alkylene structures preferably those with $C_2$ through $C_6$ alkylene building blocks and especially preferably those with $C_2$ through $C_4$ alkylene building blocks, each being substitutable with methyl groups.

As polysulfones we may mention those with $C_1$ through $C_{10}$ alkylene components and especially those which contain $C_2$ through $C_6$ alkylene building blocks and especially $C_2$ through $C_4$ alkylene building blocks whereby these can respectively also be substituted by methyl groups.

As the low molecular weight dioles those which are suitable are $C_2$ through $C_{10}$ alkyl dioles which optionally can be substituted with lower alkyl residues like $C_1$ through $C_3$ residues. In this connection ethylene glycol 1,3 propanediol 1,4-butane-diol, 1,4-bis (hydroxymethyl)cyclohexane, 1,6 hexanediol, 2,2,4-trimethyl 1,6-hexane diol, and preferably 1,4-butanediol, 1,6-hexane diol, 2,2,4-trimethyl, 1,6-hexane diol and 2,4,4-trimethyl-1,6-hexane diol; especially preferred are 1,4-butane diol and 2,2,4, trimethyl 1,6-hexanediol. It will be self understood that mixtures of the low molecular weight diols can be used.

In general, a mixture of two diols is used.

The diols can also be used in a mixture with a macro diol. of the polyester, polyether, polysiloxane or polysulphone type as has been described in detail above, whereby the polyester, polyether, polysiloxane or polysulphone can have a mean molecular weight as set forth above.

As macro diols, suitable members of this group are polycarbonates which have two OH terminal groups and an average molecular weight of $M_w$=500 to 6000 ($M_w$=average molecular weight Daltons), preferably polycarbonates with two OH terminal groups and a mean molecular weight of $M_w$=500 to 4000 (Mw=average molecular weight–Daltons), especially preferably polycarbonates with two OH terminal groups at an average molecular weight of $M_w$1000 to 3000 ($M_w$=average molecular weight), and especially preferably polycarbonates with two OH terminal groups and a mean molecular weight of $M_w$=1000-2400 ($M_w$=mean molecular weight–Daltons).

As polycarbonates those which can be mentioned have $C_1$ through $C_{10}$ alkylene building blocks, specifically those with $C_2$ through $C_6$ alkylene building blocks and especially $C_2$ through $C_4$ alkylene building blocks and whereby these each can be substituted with methyl groups. In detail mention can be made of polyethylenecarbonate, polypropylenecarbonate, polytetramethylenecarbonate, polypentamethylenecarbonate and poly-hexamethylenecarbonate.

As low molecular weight dioles the $C_2$ through $C_{10}$ alkyl dioles which can optionally be substituted with lower alkyl residues like $C_1$ to $C_3$ residues are suitable. In detail the following can be mentioned ethyleneglycol, 1,3-propanediol, 1,4-butanediol, 1,4-bis-(hydroxymethyl)-cyclcohexane, 1,6-hexane-diol, 2,4,4-trimethyl-1,6-hexanediol and 2,4,4-trimethyl-1,6-hexanediol; preferred are 1,4 butanediol, 1,6-hexanediol, 2,2,4,-trimethyl-1,6 hexane diol and 2,2,4-trimethyl-1,6 hexane diol; especially preferred are 1,4-butane diol and 2,2,4-trimethyl-1,6-hexane diol. It will be self-understood that also mixtures of low molecular weight diols can be used. In general a mixture of two diols is used. The diols can also be used in mixtures with a macro diol of the polycarbonate type as has been described in detail above and whereby the polycarbonate has a mean molecular weight as described above.

In the reaction of the prepolymer with the chain lengthener, a catalyst can be used as is known per se. As catalysts for example dibutyltindilaurate, tinoctoate or diaza-bicyclooctane can be used.

The ratio of NCO-terminal groups of the prepolymer to OH groups of the chain lengthener should in general be 1.01:1 to 1.05:1, preferably 1.02:1 to 1.04:1 and especially preferably 1.025:1 to 1.035:1.

The molecular fractionation of the method according to the invention can be carried out in a manner known per se. Suitable processes are precipitation reaction, solid phase extractions, liquid phase extractions, adsorption chromatography, precipitation chromatography in accordance with broader volumes, desorption fractionation, gel permeation chromatography (GPC) and continuous polymer fractionation (CPF); especially suitable for the molecular fractionation are precipitation reactions, gel permeation, chromatography and continuous polymer fractionation. In the molecular weight fractionation, in general, a low molecular weight component with a proportion by weight or mass of 10 to 55% by weight is separated off. Preferably the low molecular weight component with a mass proportion of 20 to 50% by weight and especially preferably with a weight mass proportion to 30 to 45% by weight is separated off and discarded.

The method according to the invention is in general carried out as follows. In a suitable apparatus, for example in a three-neck flask equipped with a stirrer, a nitrogen feed and a cooler with a drain or diversion tube, to form the prepolymer, the diisocyanate is mixed with a macrodiol and heated with continuous stirring. The temperature amounts in general to 50 to 120° C., preferably 60 to 100° C. preferably 70 to 90° C. The reaction time for the prepolymer formation was at least five hours, preferably the preopolymer formation reaction time was 10 to 20 hours and especially preferably 14 to 19 hours.

During this reaction, in a further vessel the chain lengthening agent, optionally after the addition of a catalyst, is mixed, for example, dibutyltindilaurate, tinoctoate or diaza bicyclo-octane in a manner known per se is mixed and then added to the prepolymer. As soon as prepolymer formation has terminated. Then the reaction mixture at a temperature is heated at a temperature of 50 to 120° C., preferably 60 to 100° C., especially preferably 70° to 90° C. with continuous stirring for at least 48 hours. The resulting polymer after possible deactivation of excess NCO groups with a suitable deactivation reagent, for example a secondary amine, preferably dibutylamine, is cleaned and dried. It is also possible to carry out the above described reaction in the presence of one or more solvents. Suitable solvents are dimethyl acetamide, dimethyl formamide, chloroform, methylene chloride, trichloroethylene, tetrahydrofuran and dioxane. Preferred are dimethyl acetamide, dimethyl formamide and chloroform. Especially preferred are dimethyl acetamide and chloroform. Particularly preferred as the solvent is dimethyl acetamide. If the reaction is carried out in solvent, the resulting polymer can be separated in an appropriate precipitating agent, for example isopropanol or water and separated and dried.

The obtained polymer is subjected subsequently to a molecular weight fractionation. The molecular weight fractionation will be described in detail in connection with a precipitation reaction. For that purpose the polymer is initially introduced into solution. As a solvent for the polymer, dimethyl acetamide, dimethyl formamide, chloroform, methylene chloride, trichloroethylene, tetrahydrofurane, and dioxane are suitable.

Preferred are dimethyl acetamide, dimethyl formamide and chloroform; particularly preferred is dimethyl acetamide. To the resulting polymer solution a known solvent is added slowly in a manner known per se, for example isopropanol and/or water;

Preferably isopropanol is added. In this manner the solubility of the polymer slowly decreases. As a result, molecules of the highest degree of polymerization precipitate first and those with shorter chains remain in solution. The polymer solution is held at constant temperature, for example room temperature and the precipitating agent is added with stirring. As soon as the solution becomes cloudy the temperature is raised until the precipitating polymer dissolves. Then the solution is cooled to the original temperature and the precipitating polymer is separated off and dried. Suitable combinations of solvent and precipitating agent can be readily determined by the skilled worker in the field by known procedures, by cloud titration.

The improved E-modulus obtained by the stretching treatment of the vascular prosthesis can be seen from the drawing which is a stress/extension diagram in which the amount of the extension is given in the horizontal X-direction in % and the stress in $N/mm^2$.

BRIEF DESCRIPTION OF THE DRAWING

In this diagram the measurement curve 1 shows the elasticity characteristics of a vascular prosthesis which has not been subjected to a definitive stretching. By contrast, in the measurement curve 2 the elastic properties of the same polyurethane workpieces which has been subjected to a definitive stretching has been given. From this one can clearly see that an extension of about 20% can be achieved with a 60% reduced stress. The respective low stress values which correspond to a reduced E-modulus can apply up to an extension of about 100%. Because of the improvement in the E-modulus a substantial approximation to the natural vessel or vessel wall can be achieved.

The invention claimed is:

1. A method of making a vascular prosthesis or tissue web of biocompatible polyurethane, polyamide, polysulfone, polyester, isotactic polypropylene, polynitrile or polyvinylchloride, mixtures thereof or their copolymers, with a microporous finely fibular structure, characterized by a definitive stretching (extension) with a degree of extension between 30% and 150%, and subsequent relaxation.

2. The method according to claim 1 wherein a pore size of the vascular prosthesis or of the tissue patch before the stretching is less than an extended dimension expected prior to stretching and beyond which the vascular prosthesis or tissue patch does not retract.

3. The method according to claim 1 wherein the stretching is a uniaxial or biaxial stretching.

4. The method according to claim 1 wherein the vascular prosthesis or the tissue patch prior to the stretching is soaked in polyvinylalcohol (PVA), polyvinylpyrrolidone or gelatine (collagen) that is completely or partially drawn into the vascular prosthesis or the tissue patch on an outer side thereof.

5. The method according to claim 4 wherein the stretching is carried out with an auxiliary body capable of mechanical size adjustment upon which the tissue patch is previously clamped or which is introduced into the tubular prosthesis.

6. The method according to claim 4 wherein for widening a tubular vascular prosthesis, a drawing mandrel is used.

7. The method according to claim 1 wherein the vascular prosthesis is tubular and for stretching a requisite pressure is applied from the interior with air or $N_2$, or with a liquid medium.

8. The method according to claim 7 wherein to avoid leakage, a yieldable auxiliary body is introduced into the vascular prosthesis to be stretched and is thereafter pressurized with a pressure applying medium.

9. The method according to claim 1 wherein to produce the vascular prosthesis or the tissue patch at least one aliphatic and/or at least one cycloaliphatic diisocyanate is reacted with a polyarbonate, polyester, polyether, polysiloxane, or polysulfone macrodiol with an average molecular weight of 500 to 6000, whereby the ratio of NCO terminal groups of the prepolymer to OH groups of the chain lengthening agent is 1.01:1 to 1.05:1 and a polymer obtained, optionally aftertreatment with a reagent for deactivating NCO groups which may still be present, is subjected to a molecular weight fractionation in which the low molecular weight polyurethane fraction making up 10% to 50% by weight of the polymer is separated off and discarded and the remaining high molecular weight fractionation is recovered as the biocompatible polyurethane with improved properties.

10. The method according to claim 1 wherein the degree of extension is 60% to 125%.

* * * * *